US006383506B1

(12) United States Patent
Mehta et al.

(10) Patent No.: US 6,383,506 B1
(45) Date of Patent: May 7, 2002

(54) COMPOSITIONS CONTAINING COLORANTS AND MICROORGANISMS FOR TREATING NATURAL BODIES OF WATER

(75) Inventors: Raj J Mehta; Ashok J Mehta, both of King of Prussia; Sunil Talati, Philadelphia, all of PA (US)

(73) Assignee: Organica, Inc., Norristown, PA (US)

( * ) Notice: Subject to any disclaimer, the term of this patent is extended or adjusted under 35 U.S.C. 154(b) by 200 days.

(21) Appl. No.: 09/087,746

(22) Filed: May 29, 1998

(51) Int. Cl.[7] ............................................... A01N 25/10
(52) U.S. Cl. .................... 424/408; 424/405; 435/262.5; 435/821; 504/117; 504/118
(58) Field of Search .................... 424/405, 400; 504/117, 118, 129, 150, 154; 435/262, 262.5, 821, 822

(56) References Cited

U.S. PATENT DOCUMENTS

| 4,042,367 | A | * | 8/1977 | Wilson | 504/160 |
| 4,655,814 | A | * | 4/1987 | Simpson | 71/67 |
| 5,273,749 | A | * | 12/1993 | Bok et al. | 424/405 |
| 5,492,881 | A | * | 2/1996 | Diamond | 502/401 |
| 5,679,364 | A | * | 10/1997 | Levy | 424/405 |
| 5,877,113 | A | * | 3/1999 | Mehta | 504/117 |
| 6,057,268 | A | * | 5/2000 | Mehta | 504/117 |

* cited by examiner

Primary Examiner—Neil S. Levy
(74) Attorney, Agent, or Firm—Henry E. Millson, Jr.

(57) ABSTRACT

A composition for the treatment of natural bodies of water comprising

A) beneficial aerobic microorganisms,
B) an effective quantity of at least one water-soluble colorant; and, optionally,
C) a growth accelerator for component A).

20 Claims, No Drawings

COMPOSITIONS CONTAINING COLORANTS AND MICROORGANISMS FOR TREATING NATURAL BODIES OF WATER

FIELD OF THE INVENTION

This invention relates to compositions for the treatment of natural bodies of water to control organic pollutants, algae, and/or weeds.

BACKGROUND OF THE INVENTION

Products are available commercially for the treatment of natural bodies of water to control organic pollutants and/or algae therein. Such commercial products are usually based on copper sulfate, or other heavy metal salts, which in turn results in heavy metal contamination of the water.

DESCRIPTION OF THE INVENTION

Other than in the operating examples, or where otherwise indicated, all numbers expressing quantities of ingredients or reaction conditions used herein are to be understood as modified in all instances by the term "about".

Compositions have now been discovered that overcome the above drawbacks to the use of commercial water treatment compositions containing heavy metal compounds.

The compositions of the invention contain
A) an effective quantity of beneficial aerobic microorganisms,
B) an effective quantity of at least one water soluble colorant; and, optionally,
C) an effective quantity of growth accelerators for the component A) microorganisms.

Microorganisms that can be used as component A) can be any beneficial aerobic microbial organism or combination of organisms known to control algae, weeds, and/or organic pollutants, and which can survive and function in the aqueous medium provided by natural bodies of water. Such microorganisms include but are not limited to one or more of the following bacteria:

Bacillus subtilis
Bacillus coagulans
Bacillus sphericus
Bacillus megaterium
Bacillus licheniformis
Bacillus thurirgensis
Bacillus steareothermophilus
Bacillus polymyxa
Bacillus cereus
Bacillus globigi
Bacillus halodurans
Bacillus azotofixans
Bacillus azotoformans
Azotobacter sp.
Pseudomonas flourescens
Pseudomonas aureofaciens
Saccharomyces cerevisiae
Arthrobacter sp.
Flavobacterium sp.
Streptomyces sp.

In addition to bacteria, fungi and viruses can be also used, such as Aspergillus sp., Trichoderma sp and/or other beneficial filamentous fungi.

All of the above microorganisms are well known and are readily available from public depositories including ATCC and NRRL.

The component B) water colorants diminish or prevent the penetration of sunlight into the body of water, which in turn controls algae and weed growth by preventing or minimizing photosynthesis. In addition, depending on the colors selected, the colorants can also beautify the water.

The colorants that can be used in the compositions of the invention are water soluble dyes, pigments and other coloring agents that are essentially nontoxic to fish and other desireable aquatic life. Preferred colorants are food colors, preferably those that provide a blue, blue-green, or green color to the water.

Both synthetic and naturally derived colorants can be used herein.

Among the synthetic colorants, the most useful are the FD&C food colorants, including the following blue and green dyes:

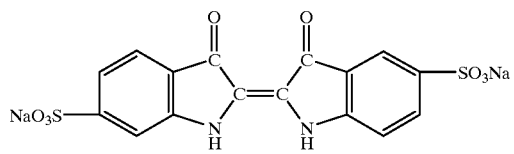

SULFONATED INDIGO COLORANT
FD&C Blue No. 2

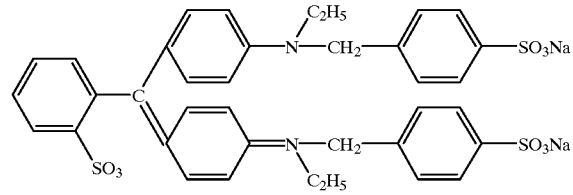

TRIPHENYLMETHANE COLORANTS
FD&C Blue No. 1
FD&C Green No. 3

Other such colorants include blue polymeric dyes, containing negatively charged solubilizing groups such as sulfonic acid groups, to impart water solubility to the polymers. Polyaminoethylene is a particularly useful polymer, having a high density of nucleophilic sites for the addition of numerous chromophores to give high color intensity per unit weight.

Other blue, green, and blue-green colorants can also be used, including other FD & C food colorants, and other colorants which have the requisite freedom from toxicity problems.

Colorants other than blue, green, or blue-green can also be used herein, although when used alone they may result in a somewhat less natural appearance to the water. However, such colorants can be used in combination with the blue, green, or blue-green colorants to provide desireable shade, tints, or hues. Such other colorants include the following:

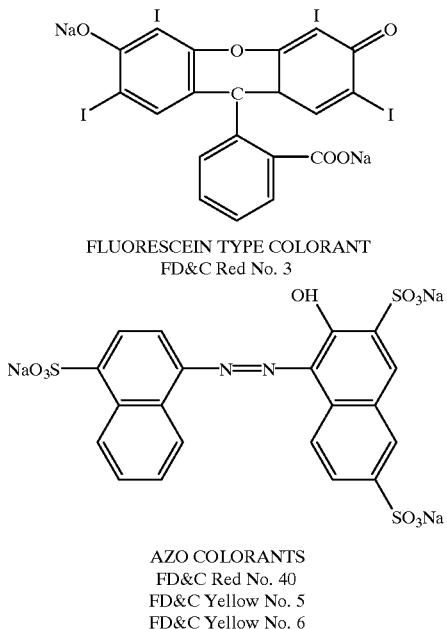

FLUORESCEIN TYPE COLORANT
FD&C Red No. 3

AZO COLORANTS
FD&C Red No. 40
FD&C Yellow No. 5
FD&C Yellow No. 6

The water colorants can also be naturally derived, including the anthocyanins, annatto colors, the betalaines, the carotenoids, cochineal, saffron, turmeric, and caramel coloring.

The anthocyanins are water soluble pigments which account for many of the red, pink, purple, and blue colors found in higher plants. However, the anthocyanins are not usually very stable, although grape anthocyanins do exhibit somewhat greater stability.

The annatto food colors are natural carotenoid colorants derived from the seeds of the tropical annatto tree, containing a highly colored resin consisting primarily of the carotenoid bixin. Annatto colors are available in water-soluble form, and range in color from yellow to orange.

The betalaines, sometimes referred to as beetroot pigments, are made up of two main groups, betacyanins (red colors) and betaxanthins (yellowish in color).

The carotenoids are tetraterpenoids consisting of eight isoprenoid residues. Hydrocarbon carotenoids are termed carotenes while oxygenated carotenoids are known as xanthophylls.

Cochineal is a red dyestuff consisting of the dried bodies of female cochineal insects.

Saffron dye is a deep orange dye obtained from the dried stigmas of saffron.

The components C) growth accelerators, which is an optional but preferred component, are organic and inorganic compounds that accelerate the growth and reproduction of the component A) microorganisms. Such growth accelerators include carbon sources such as dextrose, sucrose, molassess, and the like; combined carbon and nitrogen sources such as soy proteins, milk amino acids, yeast extracts, and the like; trace elements such as trace metals; and vitamins. In addition, some of the binders and other components used to prepare the finished solid compositions may also serve as growth accelerators for the component A) microorganisms.

When used herein, the term "natural bodies of water" includes outdoor bodies of water such as, ponds, lakes, rivers, streams, and brooks, whether naturally occurring or man made, but does not include treatment ponds and tanks for contaminated water from commercial operations such as chemical plants, sewage treatment facilities, and the like.

The relative quantities of components A) and C), when present in the compositions of the invention, are dependent in part on the quantity of microorganisms selected for component A). Preferably, component A) will consist of from $1\times10^3$ to $1\times10^9$ micro-organisms per gram of the solid form or liquid form composition and more preferably from $1\times10^4$ to $1\times10^8$ microorganisms per gram of the composition. Any quantity of component C) can be present that will effectively accelerate the growth of the microorganisms in component A) when the composition is added to a natural body of water.

The quantity of component B) in the compositions of the invention will be dependent on the particular colorant or combination of colorants selected for use, the quantity of water to be treated, and on the depth of color desired for the water.

By the term "effective quantity" used above with respect to components A) and B) is meant a quantity that will result in the elimination or reduction in the quantity of the target contaminant, i.e. algae, weeds, and/or organic pollutants. Algae and weeds are controlled by the combination of interference with photosythesis and by the pre-emptive digestion of their food sources such as nutrients containing phosphorous and/or nitrogen.

The organic pollutants that can be controlled by the solid compositions of the invention, which will also result in controlling weeds and algae, if present, include organic plant residues and toxic organic pollutants e.g. pesticides, hydrocarbons, and the like.

The compositions of the invention can be in either liquid or solid form.

Solid form compositions can be in the form of water-soluble small particulate form or in larger solid form composition. The larger solid form compositions can be made in any desired shape such as a golf ball shape, a brick shape, a donut shape, a cylinder, a square, a fish shape, a large golf tee, a large tablet, and the like.

The solid compositions of the invention are formed by combining the components into powdered, particulate, or larger solid forms of the desired shape and weight, preferably with the use of nontoxic adjuvants.

It is preferred to use water soluble or dispersible binders that are compatible with the component A) microorganisms and the component B) colorants. Suitable binders include starch (e.g. corn starch), gelatin, sugars such as sucrose, glucose, dextrose, molassess and lactose, and natural and synthetic gums such as acacia, sodium alginate, extract of Irish moss, panwar gum, ghati gum, mucilage of isapol husks, carboxmethylcellulose, methylcellulose, polyvinylpyrrolidone, Veegum® and larch arabogalacian. The binders may be present in from 1 to 95% by weight of the solid composition.

The larger solid form compositions can be prepared by compression or by the use of suitable molds.

The solid form compositions can be prepared using water as a granulating agent with e.g., pregelatinized starch as a binder. A direct compression method using dry components can also be used, with a binder such as microcrystalline cellulose, microcrystalline dextrose, amylose, or polyvinylpyrrolidone.

In addition to binders, other optional ingredients may also be present, such as lubricants, e.g. sodium benzoate, leucine, magnesium lauryl sulfate, magnesium stearate, stearic acid, hydrogenated vegetable oils and polyethylene glycol (PEG). Lubricants can be used in from 0.1 to 5% by weight of composition. One or more disintegrants can also be present such as croscarmelose, crospovidone and sodium starch glycolate, used in from 2 to 4% by weight of the composition. Other optional components include fillers.

Where the microorganisms of component A) are sensitive to light or air or to the component B) colorants or to optional added components, the microorganisms can be separately encapsulated in water soluble coatings, e.g., dyed or undyed gelatin spheres or capsules, or by microencapsulation to a free flowing powder using one or more of gelatin, polyvinyl alcohol, ethylcellulose, cellulose acetate phthalate, or sytrene maleic anhydride. The separately encapsulated microorganisms can then be mixed with the component B) colorants, the component C) growth accelerators, and any other optional components. However, encapsulation can also include components A), B), and C) if present, where compatibility is not a problem. The resulting capsules can then be mixed with one or more optional components such as binders and formed into the desired solid compositions.

The liquid, powdered, and particulate compositions are useful in relatively quiet bodies of water. For rivers, streams and other moving bodies of water, including stream fed or spring fed lakes or ponds with outlets, it is preferred to use larger solid form compositions. These larger solid form compositions are also preferred for use in relatively quiet bodies of water having large surface areas and/or relatively deep sections.

The compositions of the invention provide control of algae and weeds for much longer periods of time than is possible with the use of either component A) or B) alone. In addition, the compositions provide more complete and faster control of the algae and weeds, and are quite effective in preventing secondary algae blooms.

The invention will be illustrated but not limited by the following examples.

EXAMPLES

Example 1

About $250 \times 10^5$ spore forms of each of the following Bacillus species: *B.licheniformis, B. subtilis ,B.sphericus B. megaterium* and *B.thurirgensis*, are mixed with 180 grams of microcrystalline amylose, 8 grams of leucine, 6 grams of sodium starch glycolate, 2 grams of glucose, 2 grams of yeast extract, 1 gram of starch, 1 gram of soy peptone, and 50 grams of FD & C Blue No. 2 food color, and compressed dry in a golf ball shape mold to produce a golf ball-shaped solid composition weighing about 250 grams.

Example 2

About $500 \times 10^6$ spore forms of *Bacillus subtilis* and *Saccaromyes cerevisae*, and about $500 \times 10^6$ microencapsulated *Pseudomonas flourescens* microorganisms, are mixed with 353 grams of pregelatinized starch, 21 grams of water as a granulating agent, 19 grams of sodium benzoate, 17 grams of crospovidone, 4 grams of dextrose, 6 grams of milk amino acids, 4 grams of soy peptone, and 75 grams of a 50—50 mixture of FD &C Blue no. 1 and FD &C Green no. 3, and compressed in a brick-shaped mold to form a brick-shaped solid composition weighing about 500 grams.

Example 3

A liquid composition is prepared containing the following ingredients, per approximately 100 grams of composition:

| Ingredient | Quantity |
|---|---|
| *Bacillus coagulans* | about $100 \times 10^7$ spore forms of each |
| *Bacillus polymyxa* | |
| *Bacillus cereus* | |
| *Bacillus azatofixans* | |
| FD & C Blue No. 2 | 15 grams |
| FD & C Green No. 3 | 5 grams |
| milk amino acids | 30 grams |
| sucrose | 25 grams |
| yeast extract | 25 grams |
| trace metals | 0.01 grams |

What is claimed is:

1. A water-soluble or water-dispersible composition for the treatment of a natural body of water consisting essentially of
   A) a quantity of beneficial aerobic microorganisms that will eliminate or reduce the quantity of at least one of an organic pollutant, an algae, and a weed in at least a portion of said body of water;
   B) a quantity of at least one non-toxic water-soluble colorant sufficient to prevent or minimize the photosynthesis of at least one of an algae and a weed; and, optionally,
   C) a growth accelerating quantity of a growth accelerator for component A) that accelerates the growth and reproduction of the component A) micro-organisms.

2. The composition of claim 1 wherein the composition is in solid form.

3. The solid form composition of claim 2 wherein from $1 \times 10^3$ to $1 \times 10^9$ microorganisms per gram of composition are present in component A).

4. The solid form composition of claim 3 wherein from $1 \times 10^4$ to $1 \times 10^8$ microorganisms per gram are present in component A).

5. The composition of claim 1 wherein the microorganisms in component A) are at least one of the following:
   *Bacillus subtilis*
   *Bacillus coagulans*
   *Bacillus sphericus*
   *Bacillus megaterium*
   *Bacillus licheniformis*
   *Bacillus thurirgensis*
   *Bacillus steareothermophilus*
   *Bacillus polymyxa*
   *Bacillus cereus*
   *Bacillus globigi*
   *Bacillus halodurans*
   *Bacillus azotofixans*
   Azotobacter sp.
   *Pseudomonas flourescens*
   *Pseudomonas aureofaciens*
   *Saccaromyces cerevisiae*
   Arthrobacter sp.
   Flavobactenrum sp.
   Streptomyces sp.
   Aspergillus sp. and
   Trichoderma sp.

6. The composition of claim 1 wherein component B) is at least one colorant that provides a blue, green, or blue-green color to the water to be treated.

7. The composition of claim 6 wherein component B) is at least one Food, Drug, and Cosmetic (FD & C) food color.

8. The composition of claim 1 wherein component C) is present and comprises at least one source of carbon and nitrogen.

9. The composition of claim 8 wherein component C) contains at least one carbon source and at least one nitrogen source selected from the group consisting of dextrose, sucrose, molasses, soy proteins, milk amino acids, and a yeast extract.

10. The composition of claim 9 wherein component C) also contains at least one vitamin.

11. The composition of claim 10 wherein component C) also contains at least one trace element.

12. The composition of claim 2 wherein the composition is in the shape of a golf ball, a brick, a donut, a fish, or a large golf tee.

13. The composition of claim 1 wherein the composition controls organic pollutants, algae and weeds.

14. A method of controlling at least one of an organic pollutant, an algae, and a weed in a natural body of water by eliminating or reducing the quantity thereof comprising adding to said body of water an effective quantity of the composition of claim 1.

15. The method of claim 14 wherein the method controls organic pollutants, algae, and weeds.

16. A method of controlling at least one of an organic pollutant, an algae and a weed in a natural body of water by eliminating or reducing the quantity thereof comprising adding an effective quantity of the composition of claim 2 to said body of water.

17. A solid form composition of claim 1 wherein at least one of components A) and B) is encapsulated in a water-soluble coating in the form of spheres or capsules or microencapsulated as a free flowing powder.

18. A solid form composition of claim 17 wherein components A) and B) are encapsulated together in a water soluble coating.

19. A solid form composition of claim 1 wherein components A) and C) are encapsulated together in a water-soluble coating in the form of spheres or capsules or microencapsulated as a free flowing powder.

20. The composition of claim 1 wherein the composition consists essentially of components A), and C).

* * * * *